United States Patent
Birge et al.

(10) Patent No.: US 9,023,989 B2
(45) Date of Patent: *May 5, 2015

(54) PROTEIN-BASED PHOTOVOLTAICS AND METHODS OF USE

(75) Inventors: Robert R. Birge, Coventry, CT (US); Rekha Rangarajan, Fort Worth, TX (US)

(73) Assignee: University of Connecticut, Farmington, CT (US)

( * ) Notice: Subject to any disclaimer, the term of this patent is extended or adjusted under 35 U.S.C. 154(b) by 962 days.

This patent is subject to a terminal disclaimer.

(21) Appl. No.: 12/365,289

(22) Filed: Feb. 4, 2009

(65) Prior Publication Data

US 2009/0229669 A1 Sep. 17, 2009

Related U.S. Application Data

(60) Provisional application No. 61/029,702, filed on Feb. 19, 2008.

(51) Int. Cl.
| | |
|---|---|
| *C07K 1/00* | (2006.01) |
| *C12N 15/00* | (2006.01) |
| *C12P 21/06* | (2006.01) |
| *C12P 21/04* | (2006.01) |
| *H01L 51/00* | (2006.01) |
| *B82Y 10/00* | (2011.01) |
| *C07K 14/215* | (2006.01) |
| *H01L 51/42* | (2006.01) |

(52) U.S. Cl.
CPC ............. *H01L 51/0093* (2013.01); *B82Y 10/00* (2013.01); *C07K 14/215* (2013.01); *H01L 51/42* (2013.01); *Y02E 10/549* (2013.01)

(58) Field of Classification Search
CPC .................................................... C07K 14/215
See application file for complete search history.

(56) References Cited

U.S. PATENT DOCUMENTS

| | | | |
|---|---|---|---|
| 5,253,198 | A | 10/1993 | Birge et al. |
| 5,268,862 | A | 12/1993 | Rentzepis |
| 5,559,732 | A | 9/1996 | Birge |
| 7,109,136 | B2 | 9/2006 | Senecal et al. |
| 7,135,261 | B2 | 11/2006 | Yamazaki |
| 7,291,540 | B2 | 11/2007 | Mech et al. |
| 7,939,220 | B2 | 5/2011 | Oesterhelt et al. |
| 8,563,026 | B2 | 10/2013 | Birge et al. |
| 8,883,719 | B2 | 11/2014 | Birge et al. |
| 2006/0009805 | A1 | 1/2006 | Jensen et al. |
| 2006/0187795 | A1 | 8/2006 | Redfield et al. |
| 2009/0032683 | A1 | 2/2009 | Knopf et al. |
| 2009/0268511 | A1 | 10/2009 | Birge et al. |
| 2010/0226957 | A1 | 9/2010 | Birge et al. |
| 2010/0229384 | A1 | 9/2010 | Krulevitch et al. |

FOREIGN PATENT DOCUMENTS

| | | |
|---|---|---|
| WO | 2008141271 | 11/2008 |
| WO | 2010102205 | 9/2010 |
| WO | 2010102205 A2 | 9/2010 |

OTHER PUBLICATIONS

Branden et al. Introduction to Protein Structure, Garland Publishing Inc., New York, p. 247, 1991.*
Pfeiffer et al. Site-directed spin-labeling reveals the orientation of the amino acid side-chains in the E-F loop of bacteriorhodopsin. J Mol Biol. Mar. 19, 1999;287(1):163-71.*
Ranaghan et al. Photochemical and thermal stability of green and blue proteorhodopsins: implications for protein-based bioelectronic devices. J Phys Chem B. Nov. 11, 2010;114(44):14064-70.*
Hsu et al. Reversal of the surface charge asymmetry in purple membrane due to single amino acid substitutions. Biophys J. May 1996;70(5):2358-65.*
Sanz et al. Opening the Schiff base moiety of bacteriorhodopsin by mutation of the four extracellular Glu side chains. FEBS Lett. Jul. 30, 1999;456(1)1 91-5.*
Baliga, et al., "Genomic and genetic dissection of an archaeal regulon", PNAS Feb. 27, 2001 , vol. 98, No. 5; 2521-2525.
Bard, et al., "Artificial Photosynthesis: Solar Splitting of Water to Hydrogen and Oxygen", Acc. Chem. Res 1995 , 28; 141-145.
Birnboim, "A Rapid Alkaline Extraction Method for the Isolation of Plasmid DNA", Methods in Enzymology 1983 , vol. 100; 243-255.
Cline, Steven W. et al., "Transformation methods for halophilic archaebacteria", Can. J. Microbiol. 1989 , vol. 35, 148-152.

(Continued)

*Primary Examiner* — Yong Pak
(74) *Attorney, Agent, or Firm* — Kilpatrick Townsend & Stockton LLP

(57) ABSTRACT

Protein-based photovoltaic cells and the manufacture and use of protein-based photovoltaic cells are described. In one embodiment, bacteriorhodopsin from *Halobacterium salinarum*, which undergoes structural transitions when irradiated with a given wavelength of light, is used as the protein in the protein-based photovoltaic cells. In another embodiment, mutant bacteriorhodopsin from *H. salinarum* is used. Exposure of the protein to sunlight causes proton transfer across a membrane resulting in the generation of an electrical charge. The protein can be oriented and/or layered on a substrate and modified by mutation to enhance transmembrane proton transfer, covalent binding to a substrate and layering. The protein-based photovoltaic cells sequentially or simultaneously generate hydrogen gas from water or salt, which also can be harnessed to produce electricity.

17 Claims, 5 Drawing Sheets
(5 of 5 Drawing Sheet(s) Filed in Color)

(56) References Cited

OTHER PUBLICATIONS

Crittenden, et al., "Soft lithography based micron-scale electrophoretic patterning of purple membrane", J. Micromech. Microeng. 2005, 15; 1494-1497.
Georgescu, Radu et al., "Saturation Mutagenesis", Methods in Molecular Biology 2003, vol. 231; 75-83.
He, et al., "Oriented Bacteriorhodopsin/Polycation Multilayers by Electrostatic Layer-by-Layer Assembly", Langmuir 1998, 14; 1674-1679.
Hillebrecht, et al., "Directed Evolution of Bacteriorhodopsin for Device Applications", Methods in Enzymology 2004, vol. 388; 333-347.
Hillebrecht, Jason R. "The Characterization and Optimization of Photoactive Proteins for Performance in Optoelectronic Device Applications", A dissertation; Syracuse University 2000, 1-179.
Peck, et al., "Homologous gene knockout in the archaeon *Halobacterium salinarum* with ura3 as a counterselectable marker", Molecular Microbiology 2000, 35(3); 667-676.
Sasaki, Jun et al., "Conversion of Bacteriorhodopsin into a Chloride Ion Pump", Science vol. 269, No. 5220 (Jul. 7, 1995), pp. 73-75.
Schranz, et al., "Oriented Purple Membrane Monolayers Covalently Attached to Gold by Multiple Thiole Linkages Analyzed by Single Molecule Force Spectroscopy", Langmuir 2007, 23; 11134-11138.
Wise, et al., "Optimization of bacteriorhodopsin for bioelectronic devices", Trends in Biotechnology Sep. 2002, vol. 20, No. 9; 387-394.
U.S. Appl. No. 12/353,282, "Office Action" dated Apr. 27, 2012.
"NCBI Reference Sequence ZP_01253360", First seen on NCBI on Apr. 7, 2006 documentation in PDF format, Apr. 7, 2006.
"NCBI Reference Sequence ZP_01253360.1", Downloaded from website on Aug. 10, 2011, Apr. 7, 2006.
Bamann, Christian et al., "Spectral Characteristics of the Photocycle of Channelrhodopsin-2 and Its Implication for Channel Function", J. Mol. Biol., 2008, 375: 686-694.
Berthold, Peter et al., "Channelrhodopsin-1 Initiates Phototaxis and Photophobic Responses in Chlamydomonas by Immediate Light-Induced Depolarization", The Plant Cell, 2008, vol. 20: 1665-1677.
Bowie, et al., "Deciphering the Message in Protein Sequences: Tolerance to Amino Acid Substitutions", Science, Mar. 16, 1990, 247:1306-1310.
Bringmann, Andreas et al., "Mammalian Retinal Glial (Muller) Cells Express Large-Conductance Ca2+-Activated K+ Channels That Are Modulated by Mg2+ and pH and Activated by Protein Kinase A", Glia, 1997, 19:311-323.
Bromley, Keith M. et al., "Bio-Functional Mesolamellar Nanocomposites Based on Inorganic/Polymer Intercalation in Purple Membrane (Bacteriorhodopsin) Films", Advanced Materials, 2007, 19: 2433-2438.
Chen, Zhongping et al., "Bacteriorhodopsin oriented in polyvinyl alcohol films as an erasable optical storage medium", Applied Optics, 1991, vol. 30, No. 35, 5188-5196.
Chen, Zhongping et al., "Protein-based artificial retinas", TIBETCH, 1993, vol. 11: 292-300.
Douglass, Adam D. et al., "Escape Behavior Elicited by Single, Channelrhodopsin-2-Evoked Spikes in Zebrafish Somatosensory Neurons", Current Biology, 2008, 18: 1133-1137.
Dyukova, et al., "Optical and electrical characterization of bacteriorhodopsin films", Biosystems, 1997, 41, pp. 91-98.
Enz, Ralf et al., "Expression of the Voltage-Gated Chloride Channel CIC-2 in Rod Bipolar Cells of the Rat Retina", The Journal of Neuroscience, 1999, 19(22):9841-9847.
Essen, Lars-Oliver, "Halorhodopsin: light-driven ion pumping made simple?", Current Opinion in Structural Biology, 2002, 12:516-522.
Ettaiche, Mohamed et al., "Acid-Sensing Ion Channel 2 is Important for Retinal Function and Protects against Light-Induced Retinal Degeneration", The Journal of Neuroscience, 2004, 24(5):1005-1012.

Gillespie, Nathan B. et al., "Characterization of the Branched-Photocycle Intermediates P and Q of Bacteriorhodopsin", J. Phys. Chem, 2002, 106, 13352-13361.
Greener, Alan et al., "An Efficient Random Mutagenesis Technique Using an *E. coli* Mutator Strain", Methods in Molecular Biology, 1996, vol. 57; pp. 375-385.
He, Jin-An et al., "Bacteriorhodopsin Thin Film Assemblies—Immobilization, Properties, and Applications", Advanced Materials, 1999, 11, No. 6: 435-446.
He, Jin-An et al., "Photoelectric Properties of Oriented Bacteriorhodopsin/Polycation Multilayers by Electrostatic Layer-by-Layer Assembly", J. Phys. Chem., 1998, 102, 7067-7072.
Konnerth, A et al., "Proton-Induced Transformation of Calcium Channel in Chick Dorsal Root Ganglion Cells", J. Physiol., 1987, 386: 603-633.
Koyama, Koichi et al., "Antibody-Mediated Bacteriorhodopsin Orientation for Molecular Device Architectures", Science, 1994, 265: 762-765.
Krebs, Mark P. "Gene replacement in Halobacterium halobium and expression of bacteriorhodopsin mutants", Proc. Natl. Acad. Sci. USA, Mar. 1993, vol. 90, 1987-1991.
Krebs, Mark P., "Intramembrane Substitutions in Helix D of Bacteriorhodopsin Disrupt the Purple Membrane", J. Mol. Biol., 1997, vol. 267; 172-183.
Liu, Yunxiao et al., "Layer-by-Layer assembly of biomacromolecules on poly(ethylene terephthalate) films and fiber fabrics to promote endothelial cell growth", J. Biomed. Mater. Res., 2007, 81A: 692-704.
Liu, Yunxiao et al., "Surface modification of poly(ethylene terephthalate) via hydrolysis and layer-bylayer of chitosan and chondroitin sulfate to construct cytocompatible layer for human endothelial cells", Colloids and Surfaces, 2005, 46: 117-126.
Marc, Robert E., "Kainate Activation of Horizontal, Bipolar, Amacrine, and Ganglion Cells in the Rabbit Retina", The Journal of Comparataive Neurology, 1999, 407:65-76.
Nagel, Georg et al., "Channelrhodopsin-1: A Light-Gated Proton Channel in Green Algae", Science, 2002, vol. 296: 2395-2398.
Nagel, Georg et al., "Channelrhodopsin-2, a directly light-gated cation-selective membrane channel", PNAS, 2003, 100(24): 13940-13945.
Paula, Stefan et al., "Roles of Cytoplasmic Arginine and Threonine in Chloride Transport by the Bacteriorhodopsin Mutant D85T", Biophysical Journal, 2001, vol. 80: 2386-2395.
PCT/US2010/026362, , "International Search Report", Dec. 22, 2010.
PCT/US2010/026362, International Preliminary Report on Patentability and Written Opinion.
Peralvarez, et al., "Thr90 i s a key residue of the bacteriorhodopsin proton pumping mechanism", FEBS Letters, Elsevier, Amsterdam, NLLNKD—DOI:10.1016/50014-5793(01)03080-0, Nov. 23, 2001, vol. 508, No. 3, 399-402.
Petreanu, Leopoldo et al., "Channelrhodopsin-2-assisted circuit mapping of long-range callosal projections", Nature Neuroscience, 2007, vol. 10(5):663-668.
Phaneuf, Matthew D. et al., "Modification of Polyethylene Terephthalate (Dacron) Via Denier Reduction: Effects on Material Tensile Strength, Weight, and Protein Binding Capabilities", Journal of Applied Biomaterials, 1995, vol. 6:289-299.
Theogarajan, Luke S., "Supramolecular Architectures for Neural Prostheses", Doctoral Thesis—Massachusetts Institute of Technology, 2007, 1-230.
Varo, G et al., "Photoelectric Signals from Dried Oriented Purple Membranes of Halobacterium Halobium", Biophys. J., 1983, vol. 43: 47-51.
Verweij, J et al., "Horizontal Cells Feed Back to Cones by Shifting the Cone Calcium-Current Activation Range", Vision Res., 1996, vol. 36, No. 24:3943-3953.
Wan, Lianglu et al., "In vitro evolution of horse heart myoglobin to increase peroxidase activity", Proc. Natl. Acad. Sci. USA, Oct. 1998, vol. 95; 12825-12831.
Wen, Juan et al., "Exploring the allowed sequence space of a membrane protein", Nature Structural Biology, Feb. 1996, vol. 3, No. 2; 141-148.

(56) References Cited

OTHER PUBLICATIONS

Whaley, Sandra R. et al., "Selection of peptides with semiconductor binding specificity for directed nanocrystal assembly", Nature, Jun. 8, 2000, vol. 405; 665-668.

Wyers, Marc C. et al., "In Vivo Assessment of a Novel Dacron Surface with Covalently Bound Recombinant Hirudin", Cardiovascular Pathology, 1999, vol. 8, No. 3:153-159.

You, L et al., "Directed evolution of subtilis in E in *Bacillus subtilis* to enhance total activity in aqueous dimethylformamide", Protein Engineering, 1994, vol. 9, No. 1; 77-83.

Zhang, Yu-He et al., "Real-time Holographic imaging with a bacteriorhodopsin film", Optics Letters, 1995, vol. 20, No. 23:2429-2431.

Zrenner, Eberhart, "The Subretinal Implant: Can Microphotodiode Arrays Replace Degenerated Retinal Photoreceptors to Restore Vision?", Ophthalmologica, 2002, 216(suppl 1):8-20.

Nonfinal Office Action dated Aug. 16, 2011 in U.S. Appl. No. 12/353,282, 11 pages.

Amendment and Response to Office Action dated Feb. 16, 2012 in related U.S. Appl. No. 12/353,282, 26 pages.

Amendment and Response to Office Action dated Jul. 27, 2012 in related U.S. Appl. No. 12/353,282, 13 pages.

Notice of Allowance dated Oct. 9, 2013 in related U.S. Appl. No. 12/353,282, 10 pages.

Alexiev et al., "Rapid long-range proton diffusion along the surface of the purple membrane and delayed proton transfer into the bulk", Proc. Natl. Acad. Sci. USA, 92, 1995, 372-376.

Alexiev et al., "Evidence for Long Range Allosteric Interactions between the Extracellular and Cytoplasmic Parts of Bacteriorhodopsin from the Mutant R82A and Its Second Site Revertant R82A/G231C", Journal of Biological Chemistry, 275, 2000, 13431-13440.

Alexiev et al., "Surface Charge of Bacteriorhodopsin Detected with Covalently Bound pH Indicators at Selected Extracellular and Cytoplasmic Sites", Biochemistry, 33, 1994, 298-306.

Dale et al., "Membrane Insertion Kinetics of a Protein Domain in Vivo—The Bacterioopsin N Terminus Inserts Co-Translationally", The Journal of Biological Chemistry, 274(32), 1999, 22693-22698.

Dale et al., "Ordered membrane insertion of an archaeal opsin in vivo", PNAS, 97(14), 2000, 7847-7852.

Dunn et al., "The bacteriorhodopsin gene", Proc. Natl. Acad. Sci. USA, 78 (11), 1981, 6744-6748.

Eliash et al., "Specific Binding Sites for Cations in Bacteriorhodopsin", Biophysical Journal, 81, 2001, 1155-1162.

Hauser et al., "Interpretation of Amide I Difference Bands Observed during Protein Reactions Using Site-Directed Isotopically Labeled Bacteriorhodopsin as a Model System", J. Phys. Chem. A, 106, 2002, 3553-3559.

Heyne et al., "Reaction Control in Bacteriorhodopsin: Impact of Arg82 and Asp85 on the Fast Retinal Isomerization, Studied in the Second Site Revertant Arg82Ala/Gly231Cys and Various Purple and Blue Forms of Bacteriorhodopsin", J. Phys. Chem. B, 104, 2000, 6053-6058.

Lazarova et al., "Fourier Transform Infrared Evidence for Early Deprotonation of Asp85 at Alkaline pH in the Photocycle of Bacteriorhodopsin Mutants Containing E194Q", Biophysical Journal, 78, 2000, 2022-2030.

Martinez et al., "Subdomains in the F and G Helices of Bacteriorhodopsin Regulate the Conformational Transitions of the Reprotonation Mechanism", Proteins: Structure, Function, and Genetics, 48, 2002, 269-282.

Petkova et al., "Arginine Activity in the Proton-Motive Photocyle of Bacteriorhodopsin: Solid-State NMR Studies of the Wild-Type and D85N Proteins", Biochemistry, 38, 1999, 1562-1572.

Pfeiffer, "Studies on dynamics and function of Bacteriorhodopsin from *Halobacterium salinarum*", Dissertation: Munchen University, Herbert Utz Verlag GmbH, Munchen, Germany, 2000, p. 144.

Rink et al., "Spin-Labeling Studies of the Conformational Changes in the Vicinity of D36, D38, T46 and E161 of Bacteriorhodopsin during the Photocycle", Biophysical Journal, 73, 1997, 983-993.

Schatzler et al., "Subsecond Proton-Hole Propagation in Bacteriorhodopsin", Biophysical Journal, 84, 2003, 671-686.

Steinhoff et al., "Azide Reduces the Hydrophobic Barrier of the Bacteriorhodopsin Proton Channel", Biophysical Journal, 76, 1999, 2702-2710.

Varo et al., "Binding of Calcium Ions to Bacteriorhodopsin", Biophysical Journal, 76, 1999, 3219-3226.

Yamaguchi et al., "Surface Dynamics of Bacteriorhodopsin as Revealed by $^{13}$C NMR Studies on [$^{13}$C]Ala-Labeled Proteins: Detection of Millisecond or Microsecond Motions in Interhelical Loops and C-Terminal α-Helix", J. Biochem, 129, 2001, 373-382.

Zimanyi et al., "Pathway of Proton Uptake in the Bacteriorhodopsin Photocycle", Biochemistry, 32, 1993, 7669-7678.

Non-final Office Action dated Apr. 24, 2014 in U.S. Appl. No. 12/353,282, 5 pages.

Notice of Allowance dated Jul. 14, 2014 in U.S. Appl. No. 12/353,282, 9 pages.

\* cited by examiner

PROTEIN-BASED PHOTOVOLTAICS AND METHODS OF USE

CROSS REFERENCE TO RELATED APPLICATIONS

This application claims the benefit of U.S. Provisional Patent Application No. 61/029,702 filed Feb. 19, 2008.

STATEMENT REGARDING FEDERALLY SPONSORED RESEARCH

This invention was made with government support under Grant No. GM-34548-16/19 awarded by the National Institute of Health, Grant Nos. BES-0412387 and CCF-0432151 awarded by the National Science Foundation, and Grant No. HR0011-05-1-0027 awarded by the Federal Defense Advanced Research Projects Agency. The government has certain rights in the invention.

FIELD OF THE INVENTION

This application relates to protein-based photovoltaics and the use thereof, and more particularly relates to photovoltaics containing a rhodopsin protein or variant.

BACKGROUND

Solar power technology, or photovoltaics, is a technology that uses solar cells or solar arrays to convert light from the sun into solar-generated electricity. The manufacture and use of photovoltaic cells has expanded significantly in recent years in several countries, including the United States, due to economic incentives and advantages such as the absence of pollution during use, low operating costs, and minimal maintenance.

Solar-generated electricity is particularly useful in locations where grid connection or fuel transport is difficult, costly or impossible such as on satellites, islands, remote locations, and ocean vessels. Photovoltaics can provide a supplemental source of electricity during times of peak demand to reduce grid loading and eliminate the need for local battery power.

Virtually all commercial photovoltaic cells are based on silicon. The most efficient cells use crystalline or polycrystalline silicon as the photoactive medium. These cells are expensive to make. Cells that are made using amorphous silicon are cheaper but less efficient. Although silicon solar cells do not create pollution under operation, their manufacture is a serious source of pollution such that some environmentalists no longer consider photovoltaic energy conversion to be a "green" technology. Some photovoltaic cells include cadmium, which is a highly toxic metal that is harmful to animal life and difficult to remove from the environment. Moreover, its disposal also presents problems due to its toxicity.

Others have developed other types of photovoltaic cells using other types of compounds. For example, U.S. Pat. No. 7,109,136 to Senecal discloses electrospun conducting polymer membranes and composites that have high surface areas and are lightweight, tunable and active (electrically, chemically and optically). Senecal's electrospun conducting polymer membranes and composites are used for applications relating to ionic and electrical conductivity, photovoltaic devices, electrostatic dissipation, chemical sensing, corrosion protection, electromagnetic interference shielding and radar attenuation. Senecal further discloses an electrospinning process wherein a small amount of soluble conducting polymer is added to the polymer solutions used for spinning (known in the art as "spin dopes"). The conducting polymers of Senecal (from organic or aqueous solution or as solid dispersions) are added directly into a spin dope mixture and applied to various surfaces, such as metals, semiconductors, glass and textiles, or processed as stand alone membranes, using electro spinning technologies. U.S. Pat. No. 7,135,261 to Yamazaki discloses a multi-layered organic electrophotographic photoconductor that shows stability in mass production and adhesion ability with two layers contacting the charge generation layer. The photoconducter is free of contamination of the coating liquid for a charge transport layer during a dip-coating process due to dissolution of the charge generation layer. The multi-layered organic electrophotographic photoconductor includes a conductive substrate and an undercoat layer containing a thermosetting resin, a charge generation layer containing a charge generation material and an organic binder resin, and a charge transport layer laminated sequentially on the substrate. A disadvantage of the Yamazaki design is that its efficiency is insufficient for practical use in a photovoltaic system.

In light of the drawbacks discussed above, what is needed is a non-toxic photovoltaic technology that converts solar energy effectively and efficiently to electricity without causing pollution during or after manufacture.

SUMMARY OF THE INVENTION

Protein-based photovoltaics and the manufacture and use of protein-based photovoltaic cells are described herein. The protein in the protein-based photovoltaic cells is rhodopsin protein, preferably bacteriorhodopsin. The photovoltaics described herein here have been optimized by using variant rhodopsin proteins that enhance packing, orientation, thermodynamics and combinations thereof.

Bacteriorhodopsin mutants having particular characteristics useful for the generation of solar energy are provided. One group of mutants described herein have the ability to pump chloride anions. These bacteriorhodopsin mutants (chloride ion pump mutants) function as a chloride ion pump for brine splitting. Another group of mutants described herein have an enhanced ability to covalently attach to surfaces and particles in a manner superior to those of wild type bacteriorhodopsin molecules. These bacteriorhodopsin mutants (covalent binding mutants) have one or more amino acids replaced by cysteine residues, which provides them with enhanced abilities over wild type to covalently bind to metal surfaces and metal-coated particles such as gold surfaces and gold-coated particles. Another group of bacteriorhodopsin mutants described herein enhance the formation of orientated layers in such a way as to increase packing. These bacteriorhodopsin mutants (enhanced dipole mutants) have enhanced dipole moments, which provide increased abilities over wild type bacteriorhodopsin to generate oriented multilayers. A combination of covalent mutants and enhanced dipole mutants provides superior abilities to generate oriented bacteriorhodopsin multilayers on metal-coated surfaces and particles, particularly when the metal is gold.

BRIEF DESCRIPTION OF THE SEVERAL VIEWS OF THE DRAWINGS

The patent or application file contains at least one drawing executed in color. Copies of this patent or application publication with color drawing(s) will be provided by the Office upon request and payment of the necessary fee.

DETAILED DESCRIPTION OF THE INVENTION

Figure 1:
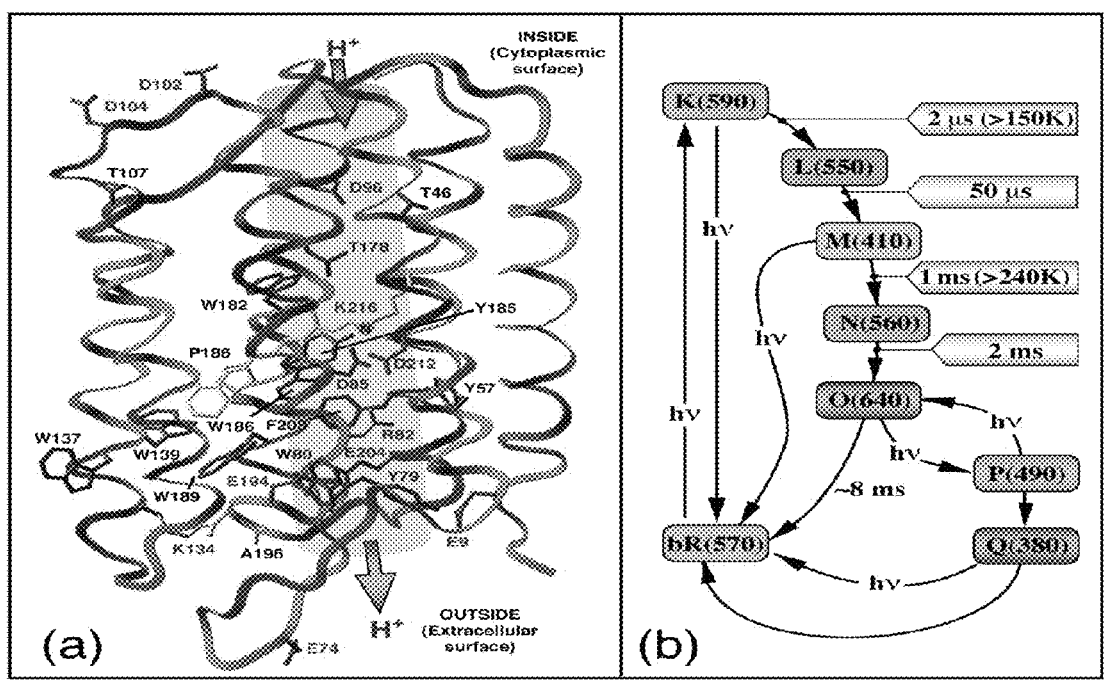
FIG. 1A is a ribbon drawing of a native bacteriorhodopsin molecule highlighting the proton channel.
FIG. 1B discloses the primary and branched photocycle of native bacteriorhodopsin showing the photointermediates and their absorption maxima in nanometers.

Protein-based photovoltaic cells, bacteriorhodopsin mutants, and the production and use of photovoltaic cells and bacteriorhodopsin mutants are described herein. The protein is a rhodopsin molecule, preferably bacteriorhodopsin. In one embodiment, the protein in the protein-based photovoltaic cells is bacteriorhodopsin. In an embodiment in which the protein is used to split brine, the rhodopsin can be halorhodopsin. In another embodiment, the protein is a bacteriorhodopsin mutant or combination of mutants that enhance packing, orientation, thermodynamics or combinations thereof. In yet another embodiment, the protein is a halorhodopsin mutant or combination of mutants that enhance orientation and packing of halorhodopsin molecules in thin films.

The bacteriorhodopsin mutants provided herein have particular characteristics useful for the generation of solar energy. One group of mutants described herein have the ability to pump chloride anions. These bacteriorhodopsin mutants (chloride ion pump mutants) function as a chloride ion pump for brine splitting. Another group of mutants have an enhanced ability to covalently attach to surfaces and particles in a manner superior to those of wild type bacteriorhodopsin molecules. These bacteriorhodopsin mutants (covalent binding mutants) have one or more amino acids replaced by cysteine residues, and these mutants have enhanced abilities over wild type to covalently bind to metal surfaces and metal-coated particles such as gold surfaces and gold-coated particles and nanotubes. Another group of bacteriorhodopsin mutants enhance the formation of orientated layers in such a way as to increase packing. These bacteriorhodopsin mutants (enhanced dipole mutants) have enhanced dipole moments, which provide increased abilities over wild type bacteriorhodopsin to generate oriented multilayers. A combination of bacteriorhodopsin mutants from both groups, i.e. covalent binding mutants and enhanced dipole mutants, provides superior abilities to generate oriented bacteriorhodopsin multilayers on metal-coated surfaces and particles.

Bacteriorhodopsin

Bacteriorhodopsin is a light-transducing protein found in Halobacteria, particularly *Halobacterium salinarum*. Altered forms of bacteriorhodopsin having modifications in the primary protein sequence are present in *H. cutirubrum* and *H. volcanii*. The bacteriorhodopsin protein, or more accurately its evolutionary ancestor, has been on the planet for 3.5 billion years and is found in and used by halobacteria to convert sunlight into energy.

*H. salinarum* is a salt marsh archaea that thrives in regions where the salt concentration is roughly five-times that of sea water. Archaea are a group of prokaryotic, single-celled microorganisms similar to bacteria.

The bacteriorhodopsin molecule undergoes structural transitions when irradiated with a given wavelength of light. It is most efficient at absorbing yellow light (wavelength 500-650 nm, with an absorption maximum at 568 nm). Bacteriorhodopsin converts sunlight to a proton gradient that can be effectively harnessed as electrical energy. In addition, when irradiated by sunlight, bacteriorhodopsin has the ability to generate hydrogen gas from water or salt, which also can be harnessed to produce electricity.

*H. salinarum* has adapted to high salt environments (5 M or 25% NaCl) and uses bacteriorhodopsin to absorb light energy and convert it to chemical energy. In response to low oxygen availability, *H. salinarum* produces a purple membrane in which thousands of bacteriorhodopsin trimers are assembled in a two-dimensional hexagonal lattice. Although bacteriorhodopsin is crucial for long-term cellular survival when oxygen is limited, the protein is not essential under aerobic conditions, because *H. salinarum* can also obtain energy from respiration.

Bacteriorhodopsin monomers form a two-dimensional crystalline lattice of trimers within the lipid bilayer of the organism. The trimeric arrangement confers thermal and chemical stability to the protein and enables it to efficiently trap sunlight in all polarizations. The primary light-absorbing moiety of bacteriorhodopsin is an all-trans retinal molecule that is covalently bound to the protein via a protonated Schiff base linkage.

DEFINITIONS

As used in this specification, the singular forms "a," "an," and "the" include plural referents unless expressly and unequivocally limited to one referent.

The terms "intrahelical loop" and "loop", as used herein, both refer to the regions of the bacteriorhodopsin protein that lie between and connect the helical segments of the bacteriorhodopsin protein.

The terms "wild type bacteriorhodopsin" and "native bacteriorhodopsin", as used herein, both refer to the form of bacteriorhodopsin as it occurs in nature. Further, as used herein, the terms "mutant bacteriorhodopsin," "mutated bacteriorhodopsin," and "bacteriorhodopsin variant" all refer to a protein in which the amino acid sequence of a wild type or native bacteriorhodopsin protein has had at least one of its amino acids replaced with a different amino acid.

Photovoltaic Cells

Photovoltaic technology utilizing one or more bacteriorhodopsin proteins as the light-transducing element and methods of use are provided. Bacteriorhodopsin from *H. salinarum*, and/or bacteriorhodopsin mutants as described herein, are used in a photovoltaic device or cell to generate electricity and also to split water into its constituent atoms to form hydrogen at one electrode and oxygen at the other electrode. The tendency of bacteriorhodopsin to split water has been considered to be a negative aspect. However, as the value of hydrogen gas as a fuel becomes more relevant, the methods described herein take advantage of this ability.

As mentioned above and shown in FIG. 1A, bacteriorhodopsin is a membrane-bound light-transducing protein that converts sunlight to a proton gradient in the purple membrane of *H. salinarum* (see FIG. 1A). Light absorption initiates a photocycle (as shown in FIG. 1B) that is coupled to structural changes in the chromophore-protein environment. The primary photochemical event involves the conversion of all-trans retinal into a high-energy cis conformation. Interactions between the chromophore and the dynamic apoprotein environment are monitored as a series of spectrally discrete intermediates labeled K, L, M, N, and O (see FIG. 1B). Each photocycle pumps a single proton across the membrane. The high quantum efficiency (0.65), cyclicity ($10^8$) and the inherent resistance of the protein to temperature, pH, gamma radiation, EMF and salt water all contribute to give the protein a comparative advantage over many other candidates for solar energy conversion. In addition, the protein can be isolated in purple membrane patches, which confers added stability and outstanding orientational homogeneity. The purple membrane patches can be placed onto surfaces to achieve thin films using known electrodeposition or electrostatic layer-by-layer methods as described, for example, by J. A. He et al., Oriented bacteriorhodopsin/polycation multilayers by electrostatic layer-by-layer assembly, *Langmuir* 14, 1674-1679, (1998); and S. Crittenden et al., Soft lithography based microscale electrophoretic patterning of purple membrane, *J. Micromech. Microeng.* 15, 1-4 (2005).

The fact that a proton, rather than an electron, is pumped adds a challenge to creating a photovoltaic system, which heretofore had not been overcome. It has been discovered that the pumping of a proton, and the resulting proton gradient, provides an optimal path to creating hydrogen gas. The produced hydrogen gas can be used as is or alternatively or additionally the proton pump can be used to generate an electrical current. As technology moves toward hydrogen based energy systems, what was once considered a disadvantage now produces a commercially viable advantage, which is used in the photovoltaic cells described herein.

Figure 2:
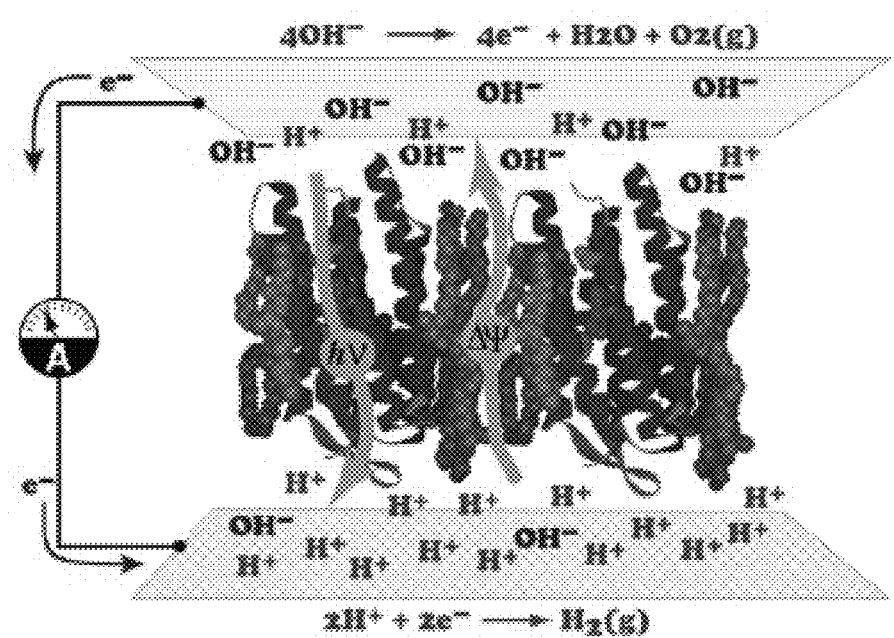
FIG. 2 is a flow chart showing an oriented bacteriorhodopsin purple membrane that photochemically translocates protons toward the extracellular electrode creating a pH gradient that can be exploited for water splitting and photovoltaic energy.

A schematic overview of the energy conversion scheme is shown in FIG. 2. A single layer of the purple membrane is shown, but in practice, multiple layers (50-300 layers) are used. The protein pumps protons to the cathode and provides $OH^-$ or $Cl^-$ ions to the anode (as shown for example in FIG. 2 and FIGS. 3A-D). The pH gradient (pH=1-4) of the oriented bacteriorhodopsin generates a photovoltaic potential of approximately 12 mV/(protein layer). This relatively large potential difference can be used to generate an electrical current.

In one embodiment, the photovoltaic cell is designed to function as a water splitting system to produce oxygen gas at the anode and hydrogen gas at the cathode, or to harness the potential to provide current.

Bacteriorhodopsin Mutants

The photovoltaic properties of bacteriorhodopsin can be enhanced by using surface-residue saturation mutagenesis and directed evolution using techniques described, for example, by K. J. Wise et al., Optimization of bacteriorhodopsin for bioelectronic devices, *Trends in Biotechnology* 20 (9), 387-394 (2002); and J. R. Hillebrecht et al., Directed evolution of bacteriorhodopsin for device applications, *Methods in Enzymology* 388, 333-347 (2004)].

Similar improvements in multilayer water splitting are effectuated by genetic modifications as described in more detail below.

In one embodiment, one or more amino acids of the amino acid sequence of the mutant bacteriorhodopsin are different from the amino acids in native bacteriorhodopsin. These substituted amino acids include one or more of the following site-directed mutagenesis members: T5X, G6X, R7X, E9X, G33X, V34X, D36X, A39X, K40X, G72X, G73X, E74X, Q75X, D85X, D96X, A103X, Q105X, K129X, V130X, Y131X, S132X, K159X, E161X, S162X, R164X, E166X, G195X, A196X, G197X, I198X, P200X, N202X, E204X, R227X, G231X, A233X, A240X, A241X, A242X, and/or A243X. In the above list, and also below, the first letter in each member represents the one letter code for the amino acid that is at that position in the native bacteriorhodopsin of *H. salinarum*. The number represents the position of the amino acid starting from the N-terminus (excluding the leader peptide), and X represents an amino acid that is different from the amino acid in the native bacteriorhodopsin.

It should be understood that any one or more of the above enumerated amino acids can be replaced to make the bacteriorhodopsin variant. For some embodiments it may be advantageous to have combinations of two or more substituted amino acids. However, there is no advantage to combining gold binding mutations on different sides of the protein, and only two site specific substitutions on any one side should be made to minimize the probability of protein interactions. Combinations involving the enhanced dipole variants should be made to enhance, not counteract, the dipole moment. Thus one would not combine substitutions that added negative charge to opposite sides, but rather make one side more negative and the other side more positive. Thus Table 3 includes information on the charge alterations associated with each variant. Combinations must be chosen to enhance the dipole moment in the desired direction by increasing negative charge on one side and increasing positive charge on the opposite side, or vice versa.

In the above enumerated variants, X is any amino acid that is different from the amino acid that it is replacing. For example, X can be any naturally incorporated amino acid (during translation), such as A, L, I, M, P, G, V, F, Y, W, S, T, C, N, Q, D, E, H, K, R, or selenocysteine (Sec or U). Alternatively, X can be any post-translationally modified amino acid, such as, for example, hydroxyproline, γ-carboxyglutamate, or O-phosphoserine.

In one variation of this embodiment, X is an amino acid that contains a conservative amino acid substitution. By conservative amino acid substitution, it is meant that an amino acid molecule with a similar side chain is substituted for the wild-type amino acid. For example, D is considered to be an acidic amino acid and can be replaced by the acidic amino acid E (or alternatively, E can be replaced by D). Similarly, L, with a hydrophobic side chain, can be replaced with any of G, A, V, M, F, W or I (or V can be replaced by any of G, A, L, M, F, W or I). Similarly, T can be replaced by S, U, or Y.

Chloride Ion Pump Mutants

In another embodiment, the bacteriorhodopsin is modified to be different from wild-type bacteriorhodopsin so that the protein pumps a chloride anion (Cl⁻) in the opposite direction from the native proton pumping while maintaining high quantum efficiency [see, for example, J. Sasaki et al., Conversion of bacteriorhodopsin into a chloride ion pump, *Science* 269, 73-75 (1995)]. This modified bacteriorhodopsin (chloride ion pump mutants) functions as a chloride ion pump and can no longer pump protons. However, the protein-based photovoltaic cells described herein provide the potential to use purple membranes containing a genetically optimized chloride ion pump for brine splitting. Various cell architectures are shown in FIGS. 3A-D. In these figures, the purple membrane layers are represented by lines to indicate ordered multilayers. The number of multilayers should and can be adjusted to yield the best compromise between optical density, output voltage and photovoltaic efficiency. The cells shown in FIGS. 3A, 3B and 3D act on water, and the cell shown in FIG. 3C works on sodium chloride.

The protein layers can be generated either by using electrophoretic deposition [see, for example, S. Crittenden et al., Soft lithography based microscale electrophoretic patterning of Purple Membrane, *J. Micromech. Microeng.* 15, 1-4 (2005)] or by electrostatic layer-by-layer deposition [see, for example, J. A. He et al., Oriented bacteriorhodopsin/polycation multilayers by electrostatic layer-by-layer assembly, *Langmuir* 14, 1674-1679, (1998)], both of which have been used to generate successful prototypes.

Figure 3:
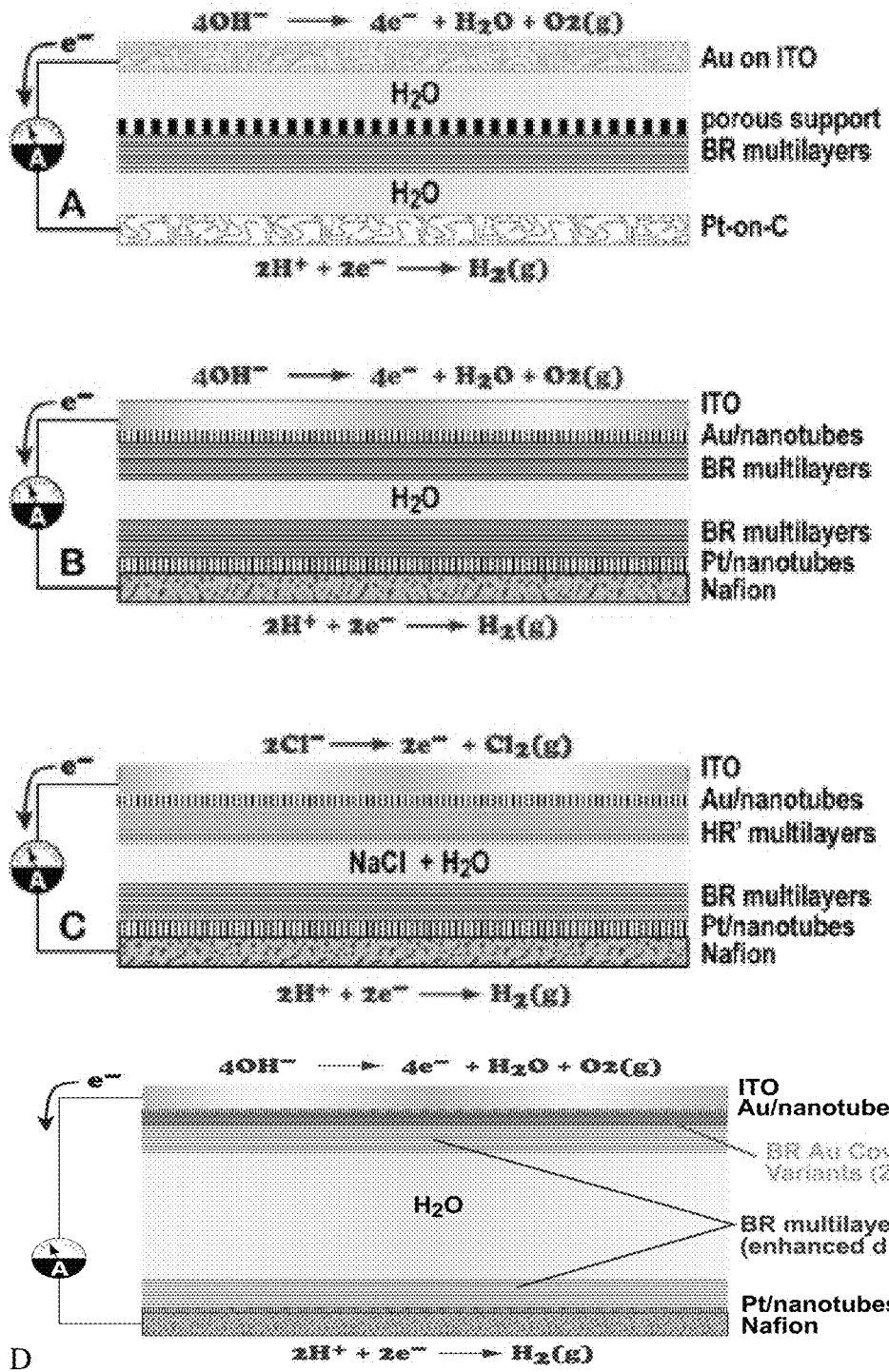
FIG. 3A is a schematic view of a photovoltaic cell wherein gold (on indium tin oxide (ITO)) is the material at the anode and platinum (on carbon) is the material at the cathode.
FIG. 3B is a schematic view of a photovoltaic cell having an ITO anode with gold nanotubes and a sulfonated tetrafluorethylene copolymer such as NAFION™ (Dupont, Wilmington, Del.) with platinum nanotubes as the cathode that is used to split water (to pump protons).
FIG. 3C is a schematic view of a photovoltaic cell having an ITO substrate with gold nanotubes as the anode and a sulfonated tetrafluorethylene copolymer such as NAFION™ with platinum nanotubes as the cathode that can pump chloride ions.
FIG. 3D is a schematic view of a photovoltaic cell having an ITO substrate with gold nanotubes as the anode and a sulfonated tetrafluorethylene copolymer such as NAFION™ with platinum nanotubes as the cathode that can split water to pump protons. Covalent bacteriorhodopsin mutants are bound to the gold nanotubes and multiple layers (50-100) of enhanced dipole bacteriorhodopsin mutants are layered on the covalent mutants and platinum nanotubes. The combination provides roughly a two-fold enhancement in the conversion efficiency of the cell.

The cell architecture shown in FIG. 3A is ideally suited for water splitting rather than for photovoltaic energy production. The more advanced cells (FIGS. 3B, 3C and 3D) use meshed CNT (carbon nanotube) electrodes with ultrahigh surface areas onto which the protein is placed. The electrochemical properties of the electrodes are enhanced by precipitating gold or platinum nanoparticles (2-10 nm) onto the CNT mesh. This approach provides sites for reversible electrode reactions while minimizing the cost by limiting the amount of noble metals used. By placing protein layers at both the anode and the cathode, the photovoltaic response of the system is increased. An individual cell has a photovoltage on the order of 2.4VDC or higher (with 100 layers of bacteriorhodopsin on each side).

The architecture shown in FIG. 3C is designed for brine splitting, which is ideally suited to conditions wherein salt water is plentiful and/or when pure water is in limited supply [see, for example, A. J. Bard et al., Artificial Photosynthesis: Solar Splitting of Water to Hydrogen and Oxygen, *Accts. of Chem. Res.* 28, 141 (1995)]. In this embodiment, the bacteriorhodopsin is genetically modified, using genetic engineering techniques known to those skilled in the art, to create a protein that is highly efficient at pumping chloride ions. In other words, the bacteriorhodopsin mutant is a chloride ion pump rather than a proton pump. Halorhodopsin is the native chloride ion pump in the purple membrane, and is a good target for modifications. However, it has been found that the native halorhodopsin does not form two-dimensional membrane arrays with the stability inherent in bacteriorhodopsin structures. Saturation mutagenesis is used to enhance the chloride ion pumping capability of variant bacteriorhodopsins. [See, for example, J. Sasaki et al., Conversion of bacteriorhodopsin into a chloride ion pump, *Science* 269, 73-75 (1995).]

Covalent Binding Mutants

In another embodiment, the bacteriorhodopsin molecule is modified to have an amino acid sequence different from wild-type bacteriorhodopsin so that the protein exhibits enhanced covalent binding to gold or gold-coated surfaces. The native bacteriorhodopsin protein generally does not automatically attach to nanotubes with the necessary alacrity. Therefore, bacteriorhodopsin covalent mutants have been made to optimize attachment to nanotubes. Variants or mutants that attach well to gold surfaces and CNTs coated with gold via covalent attachment are identified below in Table 1.

In one embodiment the following variants of bacteriorhodopsin and all possible combinations of double variants are deemed critical for binding to gold and CNTs coated with gold particles: T5C, G6C, R7C, G33C, D36C, G72C, E74C, Q75C, A103C, K129C, V130C, Y131C, S132C, E161C, S162C, R164C, E166C, I198C, P200C, N202C, E204C, G231C. Generation of triple and quadruple variants significantly decreases the binding affinity of bacteriorhodopsin to gold or CNT coated gold surfaces due to disulfide bond formation. More than two site-specific substitutions on any one side of the protein should be avoided as it can significantly increase protein-protein interactions.

In one aspect of this embodiment, bacteriorhodopsin mutants or variants are created by replacing one or more amino acids with cysteine residues. These mutants have an enhanced ability to covalently attach to metal surfaces and metal-coated particles, particularly gold surfaces and gold-coated particles, in a manner superior to those of wild type bacteriorhodopsin molecules. Exemplary mutants having this characteristic are set forth below in Table 1. Variants in which an amino acid exposed to the exterior is replaced with cysteine, particularly in the intrahelical loop region or C terminus, provide superior gold-binding characteristics.

TABLE 1

Gold-binding BR variants

| No. | Variant | Region | No. | Variant | Region |
|---|---|---|---|---|---|
| 1 | T5C | N terminus | 13 | V130C | DE loop |
| 2 | G6C | N terminus | 14 | Y131C | DE loop |
| 3 | R7C | N terminus | 15 | S132C | DE loop |
| 4 | G33C | AB loop | 16 | E161C | EF loop |
| 5 | S35C | AB loop | 17 | S162C | EF loop |
| 6 | D36C | AB loop | 18 | R164C | EF loop |
| 7 | G72C | BC loop | 19 | E166C | EF loop |
| 8 | G73C | BC loop | 20 | I198C | FG loop |
| 9 | E74C | BC loop | 21 | P200C | FG loop |
| 10 | Q75C | BC loop | 22 | N202C | FG loop |
| 11 | A103C | CD loop | 23 | E204C | FG loop |
| 12 | K129C | DE loop | 24 | G231C | C terminus |

Cysteine scanning mutagenesis of intrahelical loop region residues in bacteriorhodopsin enhances binding to gold surfaces via the formation of a covalent bond (Thio interaction).

Dipole Bacteriorhodopsin Mutants

In another embodiment, modifications are made to the bacteriorhodopsin molecule resulting in an amino acid sequence different from wild-type bacteriorhodopsin so that the protein exhibits enhanced formation of orientated layers in such a way as to increase packing. The inherent quantum efficiency of the native protein is excellent (0.65); however, manipulation of the residues on the surface of the protein provides improvements in the ability of the protein to self-assemble into multilayer systems with photovoltaic activity. Methods for the manipulation of residues are as described in, for example, J. R. Hillebrecht, The characterization and optimization of photoactive proteins for performance in optoelectronic device applications, Ph.D. Thesis, University of Connecticut, (2005).

The dipole moment mutants provide roughly a two-fold improvement in the conversion efficiency of the cell. Although not wishing to be bound by the following, it is believed that the mechanism is a combination of factors including: more complete orientation (no proteins pumping in the wrong direction) and denser packing (holes in the electrodeposition patterns are filled by proteins). Both of these effects may combine to yield higher efficiency by increasing the flux of protons and preventing back-flow, which is observed in cells that lack the enhanced dipole mutants.

Mutants, or variants, having enhanced dipole moments have increased abilities over wild type to generate oriented multilayers. The bacteriorhodopsin protein is preferably mutated in a manner that achieves between about 50 and 300 layers on a substrate. By site-directed mutagenesis, the bacteriorhodopsin is mutated so that it orients in the same direction on the substrate (for example, on a platinum or gold substrate). As an example, the bacteriorhodopsin is mutated considering such factors as Van der Waal forces, steric considerations, or ionic interactions from the side chains of the amino acids that are to be replaced so that the bacteriorhodopsin properly orients and the protein is layered to an adequate and desired depth on the substrate. Standard amino acid side chain properties are set forth in Table 2, below.

TABLE 2

Standard Amino Acid Side Chain Properties

| Amino acid | Abbreviation | Side chain polarity | Side chain acidity or basicity | Hydropathy index |
|---|---|---|---|---|
| Alanine | A | Nonpolar | Neutral | 1.8 |
| Arginine | R | Polar | Basic (strongly) | −4.5 |
| Asparagine | N | Polar | Neutral | −3.5 |
| Aspartic acid | D | Polar | Acidic | −3.5 |
| Cysteine | C | Polar | Neutral | 2.5 |
| Glutamic acid | E | Polar | Acidic | −3.5 |
| Glutamine | Q | Polar | Neutral | −3.5 |
| Glycine | G | Nonpolar | Neutral | −0.4 |
| Histidine | H | Polar | Basic (weakly) | −3.2 |
| Isoleucine | I | Nonpolar | Neutral | 4.5 |
| Leucine | L | Nonpolar | Neutral | 3.8 |
| Lysine | K | Polar | Basic | −3.9 |
| Methionine | M | Nonpolar | Neutral | 1.9 |
| Phenylalanine | F | Nonpolar | Neutral | 2.8 |
| Proline | P | Nonpolar | Neutral | −1.6 |
| Serine | S | Polar | Neutral | −0.8 |
| Threonine | T | Polar | Neutral | −0.7 |
| Tryptophan | W | Nonpolar | Neutral | −0.9 |
| Tyrosine | Y | Polar | Neutral | −1.3 |
| Valine | V | Nonpolar | Neutral | 4.2 |

Figure 4:
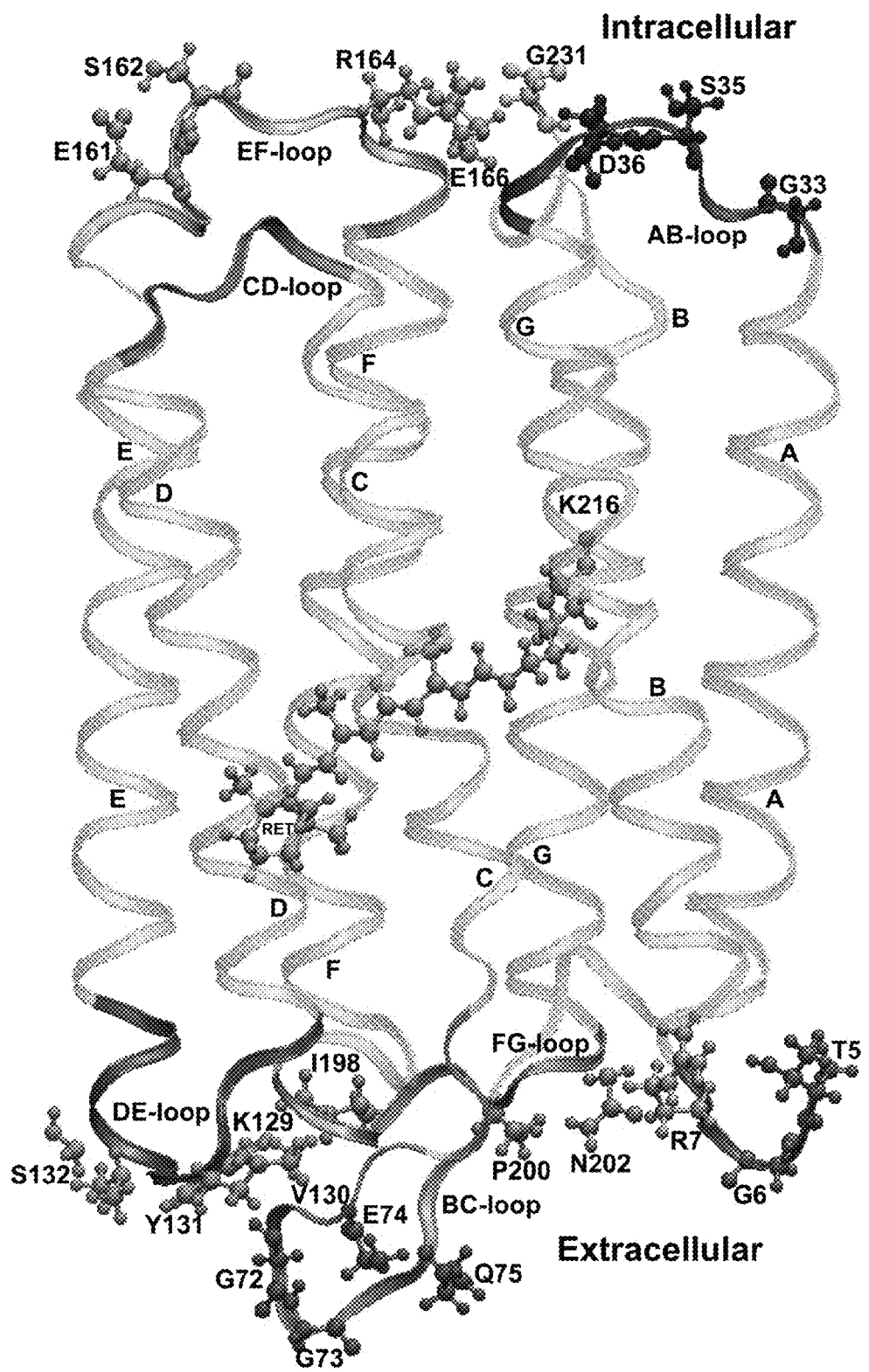
FIG. 4 is a ribbon drawing/ball and stick depiction of bacteriorhodopsin with the amino acids highlighted that can be replaced by site directed mutagenesis and also shows the retinal molecule as it exists in the native protein.
Figure 5:
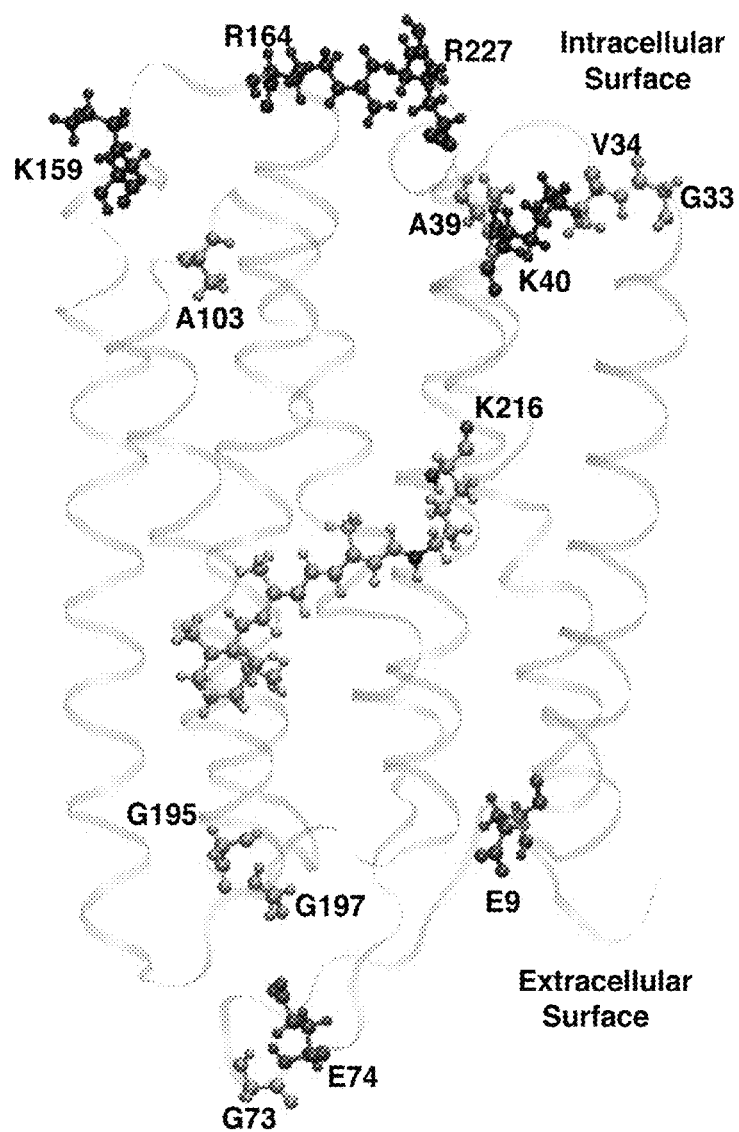
FIG. 5 is a ribbon drawing/ball and stick depiction of the intrahelical loop residues of BR based on the 1C3W (1.55 Å) crystal structure. Intrahelical loop residues in the extracellular surface are replaced with either neutral or positively charged residues, while the intrahelical loop residues in the intracellular surface are replaced with neutral or negatively charged residues to enhance proper orientation and packing of bacteriorhodopsin onto semi-conductor surfaces.

As an example, site-directed mutagenesis is used to replace the amino acid at positions R154 or G231 on the intracellular side of the protein (see FIG. 4). The relatively large side chain of R154, which contains a positive charge at physiological pH is replaced with a smaller amino acid (such as lysine, which is also positively charged at physiological pH) to take advantage of steric considerations or, alternatively, replaced with a neutral or negatively charged amino acid (such as glutamate) to change charges at the surface. Surface charges can also be manipulated by replacing a negatively charged amino acid with a neutral or positively charged amino acid or by replacing a neutral amino acid with a positively or negatively charged amino acid. These changes are useful for effectuating ionic interactions that aid the bacteriorhodopsin in orientation so that the ideal number of layers are obtained. Exemplary variants exhibiting enhanced dipole moments are set forth in Table 3, below.

TABLE 3

Enhanced Dipole Variants.

| S. No | Replacement | Position | Charge |
|---|---|---|---|
| 1 | E9Q and E9N | Extracellular | Neutral |
| 2 | G33D and G33E | Intracellular | Negative |
| 3 | V34D and V34E | Intracellular | Negative |
| 4 | A39E and A39D | Intracellular | Negative |
| 5 | K40Q and K40N | Intracellular | Neutral |
| 6 | G72K and G72R | Extracellular | Positive |
| 7 | G73K and G73R | Extracellular | Positive |
| 8 | E74Q and E74N | Extracellular | Neutral |
| 9 | A103D and A103E | Intracellular | Negative |
| 10 | Q105E and Q105D | Intracellular | Negative |
| 11 | K159Q and K159N | Intracellular | Neutral |
| 12 | R164Q and R164N | Intracellular | Neutral |
| 13 | G195K and G195R | Extracellular | Positive |
| 14 | A196K and A196R | Extracellular | Positive |
| 15 | G197K and G197R | Extracellular | Positive |
| 16 | R227Q and R227N | Intracellular | Neutral |
| 17 | A233E and A233D | Intracellular | Negative |
| 18 | A240E and A240D | Intracellular | Negative |
| 19 | A241E and A241D | Intracellular | Negative |
| 20 | A242E and A242D | Intracellular | Negative |
| 21 | A243E and A243D | Intracellular | Negative |

Plus all double, triple, quadruple, pentuple and sextuple combinations of above that, when combined, yield enhancement of the dipole moment (see text).

The protein layers shown in FIGS. 3A-D are generated either by using electrophoretic deposition or electrostatic layer-by-layer deposition as described above. The basic cell architecture shown in FIG. 3A is better for water splitting than for photovoltaic energy production. However, it is useful for both. The more advanced cells (as shown in FIGS. 3B, 3C and 3D) utilize meshed CNT electrodes with ultrahigh surface area onto which the protein is placed. The electrochemical properties of the electrodes are enhanced by precipitating gold or platinum nanoparticles (2-10 nm) onto the CNT mesh. This approach provides sites for reversible electrode reactions while minimizing the cost by limiting the amount of noble metals. By placing protein layers at both the anode and the cathode, an increase in photovoltaic response of the system is seen. In these embodiments, individual cells have photovoltages of >2.4VDC (with 100 layers of protein on each side). The architecture shown in FIG. 3C is designed for brine splitting, which is advantageous when salt water is plentiful or when pure water is in limited supply. In this embodiment, the bacteriorhodopsin molecule is genetically modified to become a chloride ion pump rather than a proton pump.

Combination Mutants

In the architecture shown in FIG. 3D, both covalent binding bacteriorhodopsin mutants and enhanced dipole bacteriorhodopsin mutants are employed in a photovoltaic cell. Variants having a combination of cysteine amino acid replacements and enhanced dipole moment amino acid replacements provide superior abilities to generate oriented bacteriorhodopsin multilayers on metal-coated surfaces and particles, such as gold.

The replacements made on the surfaces of the protein (the intracellular and extracellular sides, see FIG. 4) aid in the layering and orienting of the bacteriorhodopsin. Alternatively, replacements of the amino acids at or near the proton channel lead to a more efficient proton gradient that is useful for the development of more effective photovoltaic devices.

Mutagenesis

In one embodiment, mutants are made by performing studies in the absence of chromophore, or the bacterio-opsin polypeptide. When the system is deficient in retinal, bacterio-opsin is produced without incorporating a chromophore and provides an efficient method of generating analogue proteins with synthetically modified chromophores. The use of a bacterio-opsin-deficient cell line also aids in this process. The bacterio-opsin-deficient cell line contains a DNA insertion within the gene that encodes bacterio-opsin, bop. The production of native bacteriorhodopsin is abolished in many bacterio-opsin-deficient cell lines, allowing the expression of mutant proteins. In a variation of this embodiment, strains in which the bop gene is deleted or replaced with a selectable marker are also useful for genetic modification of bacteriorhodopsin. [See R. F. Peck et al., Homologous gene knockout in the archaeon *Halobacterium salinarum* with ura3 as a counter-selectable marker, *Mol. Microbiol.* 35, 667-676 (2000).] The principal approaches useful for the genetic engineering of proteins for photovoltaic device applications include site-directed mutagenesis, semi-random mutagenesis, random mutagenesis, directed evolution type I, and directed evolution type II. A detailed overview of the mutagenesis scheme is outlined below.

Site-Directed Mutagenesis (SDM):

Oligonucleotides with the desired mutation (eg. T5X) are purchased from Fisher Scientific at a 50 nmol synthesis scale (Fisher Scientific Company, Pittsburgh, Pa., USA). PCR reactions are carried out in a total volume of 50 μL containing: 1.0 μL of dNTP Mix®, 125 ng of mutagenic primers, 10× reaction buffer, 2.5 U of PfuTurb® DNA polymerase and 10 ng of template DNA (pBA1-bop). The thermocycling reaction is carried out under the following conditions for 18 cycles of: denaturation at 95° C. for 50 seconds; annealing at 55° C. for 50 seconds and extension at 68° C. for 5 minutes with a final extension step for 1 cycle at 68° C. for 7 minutes. The final amplification product is treated with 10 U of Dpn I enzyme and incubated at 37° C. for 1 hour. The Dpn I-treated DNA is then transformed into *E. coli* strain XL10 gold ultra-competent cells by using standard protocols. The *E. coli* transformants are grown in 5.0 mL of LB media containing 50 μg/mL ampicillin at 37° C. for 12-16 hours. Plasmid DNA is extracted by using QIAprep Spin Miniprep kit (Qiagen, Valencia, Calif., USA) as described by H. C. Birnboim, A rapid alkaline extraction method for the isolation of plasmid DNA, *Methods in Enzymology* 100, 243-255 (1983). A detailed description of the procedure can be obtained from the Quikchange® site-directed mutagenesis kit instruction manual (Stratagene cloning systems, La Jolla, Calif., USA). The pBA1 plasmid containing the mutated bop gene is sequenced with external and internal sequencing primers to confirm the identity of the gene.

Semi-Random Mutagenesis (SRM):

Semi-random mutagenesis method employs a three-step PCR reaction to introduce random nucleotide variations into a region (approximately 45 nucleotides) or a single site (3 nucleotides) in the coding region of the gene via the strand overlap extension protocol (SOE) as described by R. Georgescu et al., Saturation Mutagenesis, *Methods in Molecular Biology* 231, 75-83 (2003). In order to probe the entire mutational landscape, primers are designed with a 25% doping level. A higher doping frequency is usually employed for site-specific saturation mutagenesis (approximately 75% doping). The doped primers are synthesized with 10-15 base pair regions of homology flanking the mutated region. The SOE method uses two external primers (A and B) with restriction endonuclease sites, a doped oligonucleotide (D), and an internal primer (C) that is complementary to the 5' end of the doped oligonucleotide. All the three PCR reactions are carried out in a total volume of 50 μL containing: 1.0 μL of dNTP Mix®, 125 ng of primers, 10× reaction buffer, 2.5 U of PfuTurbo® DNA polymerase and 10 ng of template DNA. The thermocycling reaction is carried out under the following conditions for 25 cycles of: denaturation at 95° C. for 30 seconds; annealing at 52° C. for 30 seconds and extension at 72° C. for 2 minutes with a final extension step for 1 cycle at 72° C. for 10 minutes. In PCR1, primers A and C amplify the 5' end of the gene, while the 3' end of the gene is amplified in PCR2 by using primers B and D. In a final PCR reaction, the two amplification products are combined and extended by using primers A and B. The amplified bop fragments from PCR3 and the pRB1 *H. salinarum* expression vector are digested with the restriction enzymes (NheI/NcoI) to facilitate the cloning of the bop fragments into the pRB1 plasmid. Briefly, restriction digests are carried out in a final volume of 50 μL containing: 40.0 μL of PCR3, 10× multi-core buffer, 10 U of NheI, 10 U of NcoI. The samples are incubated at 37° C. for 90 minutes to ensure efficient digestion. The digested PCR products and the linearized pRB1 plasmid are electrophoresed on agarose gels. Upon excising and purifying the PCR products and the pRB1 plasmid from the agarose gels, the mutated PCR DNA is ligated into the pRB1 plasmid in a standard overnight reaction. The pRB1 plasmid is a derivative of the pBA1 plasmid and carries the LacZα stuffer fragment instead of the bop gene. Cloning of the bop variant pool into the pRB1 (pBA1+LacZα) plasmid eliminates the possibility of selecting for non-recombinant bop genes. Because pBAI contains a fully functional bop gene, it is difficult to distinguish the variant bop genes from wild type, when expressed in *H. salinarum*. The LacZα stuffer fragment renders the bop gene inactive and provides a calorimetric screen (white colonies) against non-recombinant constructs (blue colonies) in *E. coli*. The situation is somewhat different when transforming into *Halobacterium salinarum*. The white colonies (approximately 50-100) present on LB-Amp plates supplemented with IPTG and X-gal are scraped and pooled into 5 mL of LB media with ampicillin. A Qiagen® miniprep kit is then used to isolate plasmid DNA.

Strains and Media:

*H. salinarum* strain MPK-409 is provided by Mark P. Krebs (Department of Opthalmology, College of Medicine, University of Florida, FL). MPK-409 strain is cultured at 40° C. in a high-salt culture media until the $OD_{600}$ reached about 0.12-0.20. The pBA1 plasmid (SDM) and the pRB1 plasmid (SRM) containing the mutated bop gene are transformed into *H. salinarum* by using standard protocols as described by S. W. Cline et al., Transformation methods for halophilic archaebacteria, *Can. J. Microbiol.* 35, 148-152 (1989); and R. F. Peck et al., Homologous gene knockout in the archaeon *Halobacterium salinarum* with ura3 as a counter-selectable marker. *Mol. Microbiol.* 35, 667-676 (2000).

*H. salinarum* Selection and Bacteriorhodopsin Expression:

A two-step selection process is carried out to select *H. salinarum* transformants. The first selection step uses mevinolin to identify true transformants, which carry the mevinolin resistance gene encoded by the pBA1 plasmid. *H. salinarum* transformants are plated on spheroplast regeneration plates (SR-Mev) containing mevinolin (4 μg/mL) and incubated at 40° C. After 5-7 days of incubation on SR-Mev plates, colonies are resuspended in 1 mL of high salt culture media and incubated at 40° C. for 30 minutes. The cells are then spread onto solid culture media plates (CM) containing 5-fluoroorotic acid (5-FOA) and incubated at 40° C. for an additional 5-7 days. The 5-FOA selections help in the identification of true integrants that have successfully replaced the Ura3: bop locus with a functional bop gene. The 5-FOA plates are incubated under the light bank for 2-3 days to stimulate bacteriorhodopsin expression. Purple colonies are inoculated into 5.0 mL of culture media supplemented with uracil (50 μg/mL) and incubated at 40° C. at 200 rpm for 2-3 days. The cultures are serially scaled up to a final volume of 10 L of high salt media supplemented with uracil (50 μg/mL) and peptone. Incubating the cultures at 40° C. for 7-10 days under low-oxygen/high-light conditions stimulated bacteriorhodopsin production as described by Baliga N. S. et al., Genomic and genetic dissection of an archaeal regulon, *Proc. Natl. Acad. Sci. USA* 98 (5), 2521-2525 (2001).

Bacteriorhodopsin Isolation:

Bacteriorhodopsin expressing *H. salinarum* cultures are pelleted at 8,000 rpm for 15 minutes at 4° C. by using an Avanti® J-25 series centrifuge (Beckman Coulter, Inc., Fullerton, Calif., USA). The resulting pellet is resuspended in 10 mL of milli-Q-water containing DNase (0.15 mg/mL). DNase-treated protein suspensions are placed on a shaker platform and incubated at room temperature for 12-15 hours (O/N). The BR-containing purple membrane patches are subsequently purified via a series of high-speed centrifugation spins at 50,000 rpm for 35 minutes at 4° C. by using a Beckman Coulter ultracentrifuge (Beckman Coulter, Inc., Fullerton, Calif., USA).

Protein Optimization

In one embodiment, a protein-based photovoltaic device is provided in which wild-type bacteriorhodopsin is oriented on a substrate, and the oriented bacteriorhodopsin is used to convert sunlight into a proton gradient, which is harnessed as an electrical current. In a variation of this embodiment, the device also generates hydrogen gas. In a further variation, both the current and the hydrogen gas are generated simultaneously.

In another embodiment, the oriented bacteriorhodopsin is the covalent binding mutant bacteriorhodopsin described above. In a variation of this embodiment, the bacteriorhodopsin is present in between about 50 to 300 layers. In another variation, 50 to 200 layers of bacteriorhodopsin are used, and in still another variation, 100 to 200 layers are used.

In yet another embodiment, the substrate of the photovoltaic device contains gold, indium tin oxide, platinum on carbon, and/or meshed carbon nanotubes. In a variation of this embodiment, the device has an anode and a cathode wherein the anode is gold and the cathode is platinum. The bacteriorhodopsin in this variation is preferably the covalent binding mutants described above.

Method of Manufacture

A method of manufacturing a protein-based photovoltaic device is described herein. In accordance with the method, an oriented bacteriorhodopsin is deposited or layered on one or more substrates, wherein the oriented bacteriorhodopsin is used to convert sunlight into a proton gradient, which is subsequently harnessed to generate an electrical current.

In a variation of this embodiment, two substrates are employed and the oriented bacteriorhodopsin is present on one or both of the substrates. In a variation of this embodiment, the oriented bacteriorhodopsin is deposited or layered on the substrate by electrodeposition or by electrostatic layer-by-layer placement. In a further variation, the substrate contains gold, indium tin oxide, platinum on carbon and/or meshed carbon nanotubes. In another variation of the method, the bacteriorhodopsin is mutant bacteriorhodopsin. In yet another variation, the bacteriorhodopsin is between about 50 to 300 layers, 50 to 200 layers or 100 to 200 layers thick.

In a different embodiment, the oriented bacteriorhodopsin is deposited or layered on two substrates, wherein the first substrate is gold on carbon and the second substrate is platinum on carbon.

Methods of Use

The protein-based photovoltaic cell described above is useful in a method for generating electricity. In accordance with the method, electricity is generated by exposing the protein-base photovoltaic cell or device to sunlight, which causes the conversion of the chromophore, all-trans retinal, into a high-energy cis conformation, which pumps a single proton across the purple membrane, causing a large potential difference that is used to generate an electrical current.

The protein-based bacteriorhodopsin photovoltaic cell is also used in a method for generating energy by splitting water (or salt) into its constituent atoms to form hydrogen at one electrode (cathode) and oxygen (or chlorine) at the other electrode (anode). The hydrogen is then collected and used as an energy source. In one embodiment, the method is used to sequentially produce electricity and hydrogen. In another embodiment, the method is used to simultaneously produce electricity and hydrogen.

Throughout this application, various publications, patents, and/or patent applications are referenced in order to more fully describe the state of the art to which this composition and methods pertain. The disclosures of these publications, patents, and/or patent applications are herein incorporated by reference in their entireties to the same extent as if each independent publication, patent, and/or patent application was specifically and individually indicated to be incorporated by reference.

Reference is made herein to specific embodiments of the present invention. Each embodiment is provided by way of explanation of the invention, not as limitation of the invention. In fact, it will be apparent to those skilled in the art that various modifications and variations can be made in the present invention without departing from the scope or spirit of the invention. For instance, features illustrated or described as part of one embodiment may be incorporated into another embodiment to yield a further embodiment. Thus, it is intended that the present invention cover such modifications and variations as come within the scope of the appended claims and their equivalents.

Although specific embodiments of the various photovoltaic devices and methods of making them have been described, the present invention should not be construed so as to be limited to just those embodiments. It should be understood that the above examples are given only for the sake of showing that the photovoltaic cells can be made. The above devices and methods can be generalized to encompass a broad genus. In this vein, any one or more feature from any of the disclosed embodiments above can be combined with any one or more feature from any other embodiment. Accordingly, the above written description is not meant to limit the invention in any way. Rather, the below claims define the invention.

We claim:

1. An isolated modified bacteriorhodopsin protein with an amino acid sequence which, in comparison with the amino acid sequence of wild type *H. salinarum* bacteriorhodopsin protein encoded by bop gene, is modified with an amino acid substitution selected from the group consisting of G6C, R7C, E9N, G33D, G33E, V34D, V34E, A39E, A39D, K40Q, K40N, G72K, G72R, G73C, G73K, G73R, E74N, A103D, A103E, Q105E, Q105D, K159Q, K159N, R164N, G195K, G195R, A196K, A196R, G197K, G197R, R227N, A233E, A233D, A240E, A240D, A241E, A241D, A242E, A242D, A243E, A243D and a combination of two or more thereof, wherein the first letter and number in each member of the group corresponds to an amino acid in the wild type *H. salinarum* bacteriorhodopsin protein encoded by bop gene, and optionally one other amino acid substitution, wherein the modified bacteriorhodopsin protein is capable of converting sunlight into proton gradient and has a greater dipole moment than the dipole moment of the wild type *H. salinarum* bacteriorhodopsin protein.

2. The isolated modified bacteriorhodopsin protein of claim 1, wherein the one other amino acid substitution is a conservative substitution.

3. The isolated modified bacteriorhodopsin protein of claim 1, wherein the modified bacteriorhodopsin protein is bound covalently to a metal substrate.

4. The isolated modified bacteriorhodopsin protein of claim 3, wherein the metal substrate comprises platinum, gold or a gold-coated nanotube.

5. The isolated modified bacteriorhodopsin protein of claim 3, wherein a second isolated modified bacteriorhodopsin protein is bound to the metal substrate, and wherein both proteins orient in the same direction on the substrate.

6. The isolated modified bacteriorhodopsin protein of claim 3, wherein the modified bacteriorhodopsin protein is present in between about 50 and 300 layers on the substrate.

7. The isolated modified bacteriorhodopsin protein of claim 1, wherein two amino acids in the modified bacteriorhodopsin protein are replaced with two substituted amino acids that are different from that of the wild type *H. salinarum* bacteriorhodopsin protein, and wherein one of the two amino acid substitutions is selected from the group consisting of G6C, R7C, and G73C.

8. The isolated modified bacteriorhodopsin protein of claim 1, wherein the modified protein exhibits enhanced formation of orientated layers in such a way as to increase packing in comparison to the wild type *H. salinarum* bacteriorhodopsin protein.

9. The isolated modified bacteriorhodopsin protein of claim 1, comprising two amino acid substitutions, wherein one substitution is selected from the group consisting of E9N, G72K, G72R, G73K, G73R, E74N, G195K, G195R, A196K, A196R, G197K, G197R, and R227N, and wherein the other substitution is selected from the group consisting of G33D, G33E, V34D, V34E, A39E, A39D, K40Q, K40N, A103D, A103E, Q105E, Q105D, K159Q, K159N, R164N, A233E, A233D, A240E, A240D, A241E, A241D, A242E, A242D, A243E, and A243D.

10. The isolated modified bacteriorhodopsin protein of claim 1, wherein the amino acid substitution is selected from the group consisting of E9N, G33D, G33E, V34D, V34E, A39E, A39D, K40Q, K40N, G72K, G72R, G73K, G73R, E74N, A103D, A103E, Q105E, Q105D, K159Q, K159N, R164N, G195K, G195R, A196K, A196R, G197K, G197R, R227N, A233E, A233D, A240E, A240D, A241E, A241 D, A242E, A242D, A243E, A243D, and a combination of two or more thereof.

11. The isolated modified bacteriorhodopsin protein of claim 10, which contains the one other amino acid substitution selected from the group consisting of G6C, R7C, and G73C.

12. The isolated modified bacteriorhodopsin protein of claim 1, which contains a replacement with cysteine selected from the group consisting of G6C, R7C, and G73C.

13. The isolated modified bacteriorhodopsin protein of claim 12, which further contains one other substituted amino acid selected from the group consisting of E9N, G33D, G33E, V34D, V34E, A39E, A39D, K40Q, K40N, G72K, G72R, G73K, G73R, E74N, A103D, A103E, Q105E, Q105D, K159Q, K159N, R164N, G195K, G195R, A196K, A196R, G197K, G197R, R227N, A233E, A233D, A240E, A240D, A241E, A241 D, A242E, A242D, A243E, and A243D.

14. The isolated modified bacteriorhodopsin protein of claim 1, wherein the amino acid substitution is selected from the group consisting of E9N, G33D, G33E, V34D, V34E, A39E, A39D, K40Q, K40N, G72K, G72R, G73K, G73R, E74N, A103D, A103E, Q105E, Q105D, K159Q, K159N, R164N, G195K, G195R, A196K, A196R, G197K, G197R, R227N, A233E, A233D, A240E, A240D, A241E, A241D, A242E, A242D, A243E, A243D, and double, triple, quadruple, pentuple and sextuple combinations thereof.

15. An isolated modified bacteriorhodopsin protein with an amino acid sequence which, in comparison with the amino acid sequence of wild type *H. salinarum* bacteriorhodopsin protein encoded by bop gene, is modified with one or more amino acid substitution selected from the group consisting of E9N, G33D, G33E, V34D, V34E, A39E, A39D, K40Q, K40N, G72K, G72R, G73K, G73R, E74N, A103D, A103E, Q105E, Q105D, K159Q, K159N, R164N, G195K, G195R, A196K, A196R, G197K, G197R, R227N, A233E, A233D, A240E, A240D, A241E, A241D, A242E, A242D, A243E and A243D, wherein the first letter and number in each member of the group corresponds to an amino acid in the wild type *H. salinarum* bacteriorhodopsin protein encoded by bop gene, wherein the modified bacteriorhodopsin protein is capable of converting sunlight into proton gradient and wherein the modified bacteriorhodopsin protein has a greater dipole moment than the dipole moment of the wild type *H. salinarum* bacteriorhodopsin protein.

16. An isolated modified bacteriorhodopsin protein with an amino acid sequence which, in comparison with the amino acid sequence of wild type *H. salinarum* bacteriorhodopsin protein encoded by bop gene, is modified with an amino acid substitution selected from the group consisting of E9N, G33D, G33E, V34D, V34E, A39E, A39D, K40Q, K40N, G72K, G72R, G73K, G73R, E74N, A103D, A103E, Q105E, 0105D, K159Q, K159N, R164N, G195K, G195R, A196K, A196R, G197K, G197R, R227N, A233E, A233D, A240E, A240D, A241E, A241D, A242E, A242D, A243E, A243D, and double, triple, quadruple, pentuple and sextuple combinations thereof, wherein the first letter and number in each member of the group corresponds to an amino acid in the wild type *H. salinarum* bacteriorhodopsin protein encoded by bop gene, wherein the modified bacteriorhodopsin protein is capable of converting sunlight into proton gradient and wherein the dipole moment of the modified bacteriorhodopsin protein is greater than the dipole moment of the wild type *H. salinarum* bacteriorhodopsin protein.

17. The isolated modified bacteriorhodopsin protein of claim 12, wherein the substituted cysteine is bound covalently to a metal surface.

\* \* \* \* \*